US010825329B2

(12) United States Patent
Katz et al.

(10) Patent No.: US 10,825,329 B2
(45) Date of Patent: Nov. 3, 2020

(54) IDENTIFYING DATA OF A PERSON USING OF A PERSONAL EMERGENCY DEVICE

(71) Applicant: Essence SmartCare Ltd, Herzeliya Pituach (IL)

(72) Inventors: Barak Katz, Petach Tiqwa (IL); Alon Yechezkel Biran, Tel Aviv-Jaffa (IL); Yaron Oppenheim, Herzliya (IL)

(73) Assignee: ESSENCE SMARTCARE LTD, Herzliya Pituach (IL)

( * ) Notice: Subject to any disclaimer, the term of this patent is extended or adjusted under 35 U.S.C. 154(b) by 0 days.

(21) Appl. No.: 16/429,858

(22) Filed: Jun. 3, 2019

(65) Prior Publication Data

US 2019/0371158 A1 Dec. 5, 2019

(30) Foreign Application Priority Data

Jun. 4, 2018 (LU) ........................................ 100820

(51) Int. Cl.

*G08B 25/01* (2006.01)
*G06Q 50/26* (2012.01)
*G08B 25/10* (2006.01)

(52) U.S. Cl.

CPC ......... *G08B 25/016* (2013.01); *G06Q 50/265* (2013.01); *G08B 25/10* (2013.01)

(58) Field of Classification Search

CPC ....... G06Q 50/265; G08B 25/10; G16H 10/60
See application file for complete search history.

(56) References Cited

U.S. PATENT DOCUMENTS

2014/0253326 A1* 9/2014 Cho ........................ G08B 7/066 340/539.13
2015/0154364 A1 6/2015 Biasi et al.

OTHER PUBLICATIONS

Foreign Communication from a Related Counterpart Application, Luxembourg Search Report and Written Opinion dated Feb. 26, 2019, Luxembourg Application No. 100820 filed on Jun. 4, 2018.

* cited by examiner

*Primary Examiner* — Omeed Alizada

(57) ABSTRACT

In this disclosure, a person may be identified by: (i) receiving a first message comprising an ID of a first device and a hardware ID of a personal emergency device; (ii) linking the personal emergency device with personal data of the person, the personal data being associated with the ID of the first device; and (ii) receiving a second message from a mobile device comprising the hardware ID of the personal emergency device. In response to receiving the second message, and/or receiving a subsequent message received via the mobile device and comprising the hardware ID of the personal emergency device, a message is transmitted to a monitoring station based on the prior association of the personal data with the hardware ID of the personal emergency device. The message includes the personal data or an identifier for identifying said personal data.

18 Claims, 3 Drawing Sheets

IDENTIFYING DATA OF A PERSON USING OF A PERSONAL EMERGENCY DEVICE

CROSS-REFERENCE TO RELATED APPLICATIONS

The present application claims priority to Luxembourg Application No. LU100820 filed with the Intellectual Property Office of Luxembourg on Jun. 4, 2018 which is incorporated herein by reference in its entirety for all purposes.

TECHNICAL FIELD

The present invention relates to a method, computer product and a system for identifying to a monitoring station personal data of a person in response to a use of a personal emergency alert device. The data is linked, in a server, to a first device, and person may be associated with the first device, the personal emergency device, and a mobile device. In some embodiments, the invention may be used to monitor the safety/health of the person.

BACKGROUND

Personal emergency devices may be carried and/or worn by a person for their safety. Threats to their safety may be from another person or from a state of their health and/or physical condition. Such devices may be used by the elderly, for example. Such a device may monitor a person's safety by including a panic detector or button and/or fall detector, and transmitting an alert message, which is directly or indirectly received by a monitoring station.

For the monitoring station to act on any received alerts, they need to know details about the person, such as any one or more (including potentially all) of: as who they are, where they live, where they are currently located, how old they are, their medical history and/or a relative of the person, and suchlike.

However, there may be problems and/or challenges in determining such information. For example, a personal emergency device may transmit an alert to a phone which then automatically calls a monitoring station. An attendant at the monitoring station then needs to ask the person their personal details, but the person may not be able to tell the attendant this information, for example due to incapacitation. One solution is to register this information beforehand. For example, the details may be typed by the person into an app on the person's smartphone, which interfaces between the personal emergency device and the monitoring station. However, this can be difficult for some people, especially elderly people, who may not be technologically literate or able.

Reference to any prior art in this specification is not an acknowledgement or suggestion that this prior art forms part of the common general knowledge in any jurisdiction, or globally, or that this prior art could reasonably be expected to be understood, regarded as relevant/or combined with other pieces of prior art by a person skilled in the art.

SUMMARY OF THE INVENTION

In a first aspect the invention provides a method of identifying to a monitoring station personal data of a person in response to a use of a personal emergency alert device, wherein the personal data is linked, in a server, to a first device, the method comprising:

a. receiving, at the server, a first message comprising an ID of the first device and a hardware ID of the personal emergency device;
b. linking, at the server, the personal emergency device with the personal data, by:
   i. identifying the personal data corresponding to the received ID of the first device,
   ii. associating the personal data with the hardware ID of the personal emergency device;
c. receiving, at the server, a second message from the mobile device comprising the hardware ID of the personal emergency device; and
d. in response to at least one of (i) receipt of the second message, and (ii) receipt of a subsequent message received at the server via the mobile device and comprising the hardware ID of the personal emergency device, transmitting, by the server, a message to the monitoring station, wherein based on the prior association of the personal data with the hardware ID of the personal emergency device the server includes in the message (i) the personal data or (ii) an identifier for identifying said personal data.

In a second aspect the invention provides a method of identifying and enabling the accessing of personal data of a person that is linked to a first device wherein the personal data is to be identified and accessed for use of a plurality of additional devices including a personal emergency device and a mobile device, the method comprising:

a. receiving, at a server, a first message comprising an ID of the first device and a hardware ID of the personal emergency device;
b. linking, at the server, the personal emergency device with the personal data, by:
   i. identifying the personal data corresponding to the received ID of the first device,
   ii. associating the personal data with the hardware ID of the personal emergency device;
c. receiving, at the server, a second message from the mobile device comprising the hardware ID of the personal emergency device, wherein at least one of (i) receipt of the second message, and (ii) receipt of a subsequent message received via the mobile device and comprising the hardware ID of the personal emergency device, is used to access the personal data based on the prior association of the personal data with the hardware ID of the personal emergency device.

For each of the above aspects of the invention, the second message may further comprise an ID of the mobile device, and step (b)(ii) may further comprise associating the personal data with the ID of the mobile device, wherein a subsequent message received from the mobile device must comprise the hardware ID of the personal emergency device and the ID of the mobile device for the server transmit said message to the monitoring station in response to receiving the subsequent message.

The second message may further comprise an ID of the mobile device, and the method may further comprise associating the personal data with the ID of the mobile device. In some embodiments, the subsequent message further comprises the ID of the mobile device. In some embodiments, said message transmitted to the monitoring station is based on the subsequent message received from the mobile device comprising both the hardware ID of the personal emergency device and the ID of the mobile device.

In some embodiments, the ID comprises application ID of a monitoring application installed on the mobile device, a hardware ID of the mobile device, and/or a mobile number of the mobile device, but in any case, the message transmitted to the monitoring station may comprise a mobile number of the mobile device.

In some embodiments, wherein first and second messages are received within a time window of a predetermined duration to enable step (b). In some embodiments, the server forwards the details of the linked devices to one or more remote devices.

In some embodiments, the first device is a control panel, the personal emergency device is a battery operated wearable device which preferably includes a fall detector and a panic detector. In some embodiments, the personal emergency device wirelessly communicates with the first device in a pairing process that triggers said first message from the first device. By such pairing the personal emergency alert device and the first device exchange their respective IDs, so both devices become known to each other.

In some embodiments, the personal emergency device communicates with the mobile device via a Bluetooth communication, said communication triggering transmission of said second message to server from the mobile device. The communication with the mobile device is in come embodiments a Bluetooth communication, more specifically a Low Energy Bluetooth (BLE) advertisement, which is a one way communication, broadcasted from the personal emergency alert device.

In some embodiments, the personal emergency device is configured to, in response to detecting a fall or panic event, transmit a Bluetooth signal, e.g. a BLE advertisement, which includes the hardware ID of the personal emergency device for receipt by mobile device for the mobile device to transmit said subsequent message to the server.

In some embodiments, said personal data is stored as a record at the monitored station, wherein the monitoring station uses said identifier for identifying said personal to access said personal data by retrieving said personal data from the record at the monitoring station.

In some embodiments the server accesses the personal data from a memory associated with the sever.

In some embodiment, the message transmitted to the monitoring station further comprises data related to an event detected by the personal emergency device. The data related to the event may be derived from the subsequent message.

In some embodiments of the invention, the first message is received from the first device.

According to a third aspect of the invention there is provided a system for identifying personal data of a person in response to a use of a personal emergency alert device, wherein the personal data is linked, in a server, to a first device, the first device being a server and the system including the server, the server being programmed to:

a. receive a first message comprising an ID of the first device and a hardware ID of the personal emergency device,
b. link the personal emergency device with the personal data, said linking including:
   i. identifying the personal data corresponding to the received ID of the first device,
   ii. associating the personal data with the hardware ID of the personal emergency device;
c. receive a second message from the mobile device comprising the hardware ID of the personal emergency device; and
d. in response to at least one of (i) receipt of the second message, and (ii) receipt of a subsequent message received via the mobile device and comprising the hardware ID of the personal emergency device, transmitting a message to the monitoring station wherein based on the prior association of the personal data with the hardware ID of the personal emergency device the server includes in the message (i) the personal data or (ii) an identifier for identifying said personal data.

According to a fourth aspect of the invention there is provided a system for identifying and enabling the accessing of personal data of a person that is linked to a first device wherein the personal data is to be identified and accessed for use of plurality of additional devices including a personal emergency device and a mobile device, the system including a server, the server being programmed to:

a. receive a first message comprising an ID of the first device and a hardware ID of the personal emergency device,
b. link the personal emergency device with the personal data, said linking including:
   i. identifying the personal data corresponding to the received ID of the first device,
   ii. associating the personal data with the hardware ID of the personal emergency device;
c. receive a second message from the mobile device comprising the hardware ID of the personal emergency device, wherein at least one of (i) receipt of the second message, and (ii) receipt of a subsequent message received via the mobile device and comprising the hardware ID of the personal emergency device, is used to access the personal data based on the prior association of the personal data with the hardware ID of the personal emergency device.

In the third and/or fourth aspects of the invention, the server may be a server that is configured to execute the first or second aspect of the present invention.

In some embodiment the system consists of the server, which in other embodiments, the system includes other one or more devices, which may include any one or more of: the personal emergency alert device, the monitoring station and the mobile device.

The invention extends in one aspect to a computer product comprising one or more computer readable mediums storing a plurality of instructions for controlling a electronic system to perform an operation of any of the described methods.

According to another aspect of the invention there is provided a computer program product comprising one or more computer readable mediums storing a plurality of instructions which when executed by a server perform any of the described methods.

Other embodiments of the invention will be appreciated from the figures and description which follows.

One or more embodiments of the present invention use a message from a first device to an application server to associate the personal emergency device with the first device, wherein the details of the person have already been registered in a database and are electronically retrievable by the application server. The message is known to be from the first device because of an already registered identifier associated with the first device. Based on the association between the first device and the personal emergency device (by virtue of the message) the server may link to the registered personal details a unique identifier (e.g. a serial number) of the personal emergency device that is received in the message.

Based on the now registered identifier of the personal emergency device, the person using the personal emergency device, and the personal details of the person, are then identifiable from alert messages sent from an unknown mobile communications device, where such messages a transmitted in response to an alert received, by the mobile communications device, from the personal emergency device. Further, an identifier associated with that mobile communications device may also automatically be registered by its association with the identifier of the personal emergency device, the association being by virtue of both identifiers being received in a message from the mobile communications device.

Subsequent alert messages from the mobile communications device and including the registered identifiers of the mobile communications device and the personal emergency device enable, inform the server that the alert came from that specific personal emergency device from that mobile communications device. In some embodiments, the server may then initiate an action, such as informing a monitoring station of the alert, in such a manner that the monitoring station may know the details of the person and may also know the current mobile communications device in the person's possession. In embodiments in which the mobile phone number is associated with the registered mobile identifier, the personal details of the person may automatically be accessed by a monitoring station if the monitoring station receives an incoming call from that phone number.

Advantageously, a person does therefore not need to actively supply their personal details for the personal emergency device, nor do they need to actively supply their personal details for the mobile phone (except in some embodiments where they may enter their phone number, as will be described). The personal details only needed to be provided to register the first device.

In some embodiments, the unique identifier of the personal emergency device is communicated to the server upon an RF pairing between the personal emergency device and mobile communications device. In lieu of BLE other short-range, preferably low power, communication protocols may be employed for communications between the personal emergency device and the first device. In some embodiments communications between the personal emergency device and the first device is via a protocol that operates in a sub-gigahertz frequency range. Further, advantageously a single action at the personal emergency device may be used to trigger the personal emergency device to undertake both the communication with the first device and the communication with the mobile device to provide the ID of the personal emergency device to both the first device and the mobile device for system configuration, thus making for a simple setup process.

The first device is in some embodiments a device of a home monitoring system, e.g. it may be a control panel which communicates with a plurality of peripheral monitoring devices, such as voice-activated panic detectors and/or motion sensors.

As used herein, except where the context requires otherwise, the terms "comprises", "includes", "has", and grammatical variants of these terms, are not intended to be exhaustive. They are intended to allow for the possibility of further additives, components, integers or steps.

Various embodiments of the invention are set out in the claims at the end of this specification. Further aspects of the present invention and further embodiments of the aspects described in the preceding paragraphs will become apparent from the following figures and description, given by way of non-limiting example only. As will be appreciated, other embodiments are also possible and are within the scope of the claims.

DETAILED DESCRIPTION OF THE EMBODIMENTS

Figure 1:
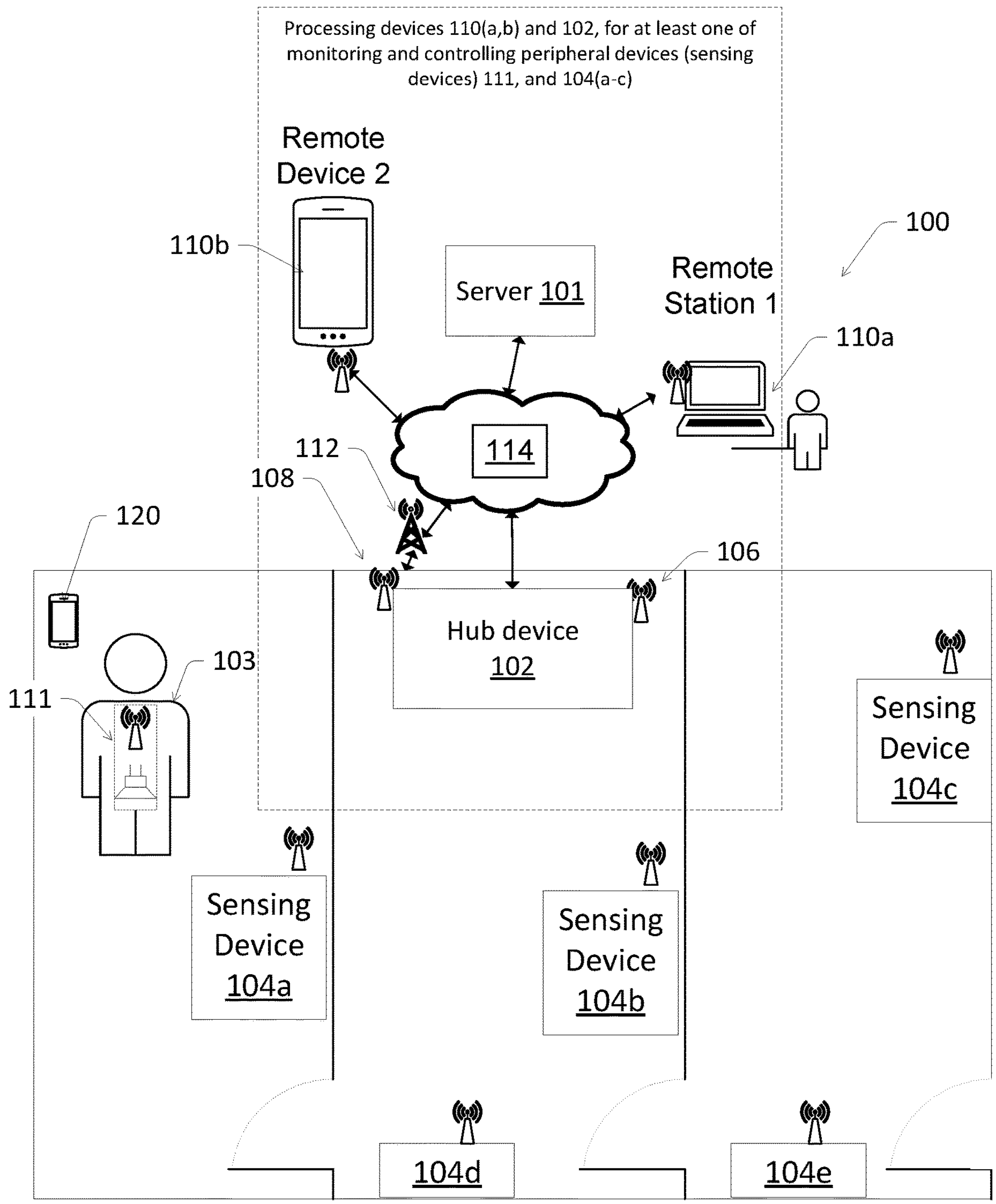
FIG. 1 shows a schematic block diagram of an embodiment of a system for identifying to a monitoring station personal data of a person who is associated with multiple devices including a first device linked to the personal data of the person and a plurality of additional devices.

An exemplary embodiment of a system 100 in accordance with an aspect of the present invention is illustrated in FIG. 1. In this example the system is a monitoring system that includes home monitoring devices. The system 100 has a hub device 102 in the form of a control panel that provides central control of, and data collection from, a plurality of peripheral devices 104(*a-e*) by RF communication using a local-communication antenna 106 on the control panel 102.

The peripheral devices may include passive infrared detectors (PIRs) 104(*c,d*) for detecting the presence of a person in a corresponding monitored space with the environment, such as in a specific room. Other peripheral devices, such as other peripheral device 104*e*, may be or include, for example, motion sensors, sensors for detecting changes in a state of a door or window, temperature sensors or any other sensor for measuring an environmental condition or an indication relating to a person 103 that may be in the environment. The other peripheral devices may alternatively be any other smart device for assisting living, including a smart TV, one or more lights, an air conditioning or heating system a hi-fi sound-system, and the like.

The person 103 may be someone for whom monitoring is desirable or necessary. For example, the person 103 may be an elderly or infirm person, and the environment in which they are monitored may be a home residence, in which there may rarely, or at least not always, be another person present to see that the person 103 is safe and well.

The system 100 provides an ability for the person 103 to send an alert to a remote station 110(*a,b*) indicating a threat to their safety, which may be an environmental threat or a threat to their health or mobility. For example each of the control panel 102 and the peripheral devices 104(*a,b*) may include one or more distress actuators (e.g. a panic button and a panic pull chord) and may include a microphone for detecting a spoken call for help or a threat-indicative sound. Such devices 104(*a,b*) may be referred to as voice panic detectors (VPDs)

The peripheral devices 104(*a,e*) communicate messages to and from the control panel 102, by radio frequency (RF) communication (in some embodiments is in a sub-gigahertz frequency range), and thus the control panel 102 has one or more RF antennas 106 for the such local-communication. One or more of the RF antennas 106, or one or more other antennas, of the control device may optionally be enabled for Low Energy Bluetooth (BLE) communication. BLE signals and/or other RF signals may be received from a portable, body-worn personal emergency device 111 which includes distress detection and fall detection (e.g. based on an accelerometer) when worn on the person 103. In some embodiments such other RF signals are in a sub-gigahertz frequency range. Distress detection is achieved by means of distress/panic button. Optionally, the portable personal emergency device may additionally or alternatively detect other personal emergencies based on medical/health parameters, e.g. heart rate, for example. In some embodiments, in which the personal emergency device 111 detects is equipment with at least fall and distress detection, the personal emergency device 111 may advantageously be a pendant. In other embodiments personal emergency device 111 may take the form of any other portable device which may be worn on a person in a manner that is easily accessible, including on the wrist.

To use the personal emergency device 111 in the monitored space, the emergency device 111 is, for first use, paired with the hub device 102 using RF communications. During the pairing process a unique hardware identifier, such as a serial number, of the emergency device 111 is communicated to the hub device 102. This hardware identifier is relayed, by the hub 102, to the server 101. The server 101 more particularly, receives a message (e.g a packet or a plurality of associated packets) that includes both an identifier of the hub device 102 (e.g. a hardware identifier, such as a serial number) and a hardware identifier (e.g. a serial number) of the personal emergency device 111.

Upon receiving the communication, the server associates the hardware identifier of the device 111 with a database entry including the details of the person 103, the personal details corresponding to the received identifier of the hub device 102. The details include, in this exemplary embodiment, who they are, where they live, where they are currently located, how old they are, their medical history and/or a relative of the person, and suchlike.

Thereafter, during use of the personal emergency device 111 with the hub 102, in an event that a safety-threat condition is detected/sensed by the personal emergency device 111, the personal emergency device 111 transmits an RF signal which includes its hardware identifier and this RF signal is received by the hub device 102. Upon receiving the RF signal, an alert signal including the hardware identifier is transmitted, from the hub device 102 to the server 101, which acts as needed, e.g. by transmitting a corresponding alert signal to one or both of the monitoring devices/stations 110(*a,b*). In some embodiments the corresponding alert signal includes the person's personal details (e.g. as listed above), retrieved from the database entry for the device 111, based on the received hardware identifier of the device 111. The personal details may include a mobile phone number on which to contact the person 103, which may be automatically entered into a dialer. In other embodiments, as will be described below, an account record with such personal details is transmitted from the server 101 to monitoring station 110(*a*) when the hardware ID of emergency device 111 is first received, and when an alert including the hardware ID of emergency device 111 is later received by server 101, the server transmits a reference to that record in the corresponding alert to the remote station 110*a*, which is a computing device. A person attends to the monitoring station 110*a* to respond as needed to incoming notifications and/or calls.

The control panel has a second antenna 108 that may be used for the communication with one or more remote stations 110(*a,b*) and/or a distinct server 101, the communication via the second antenna being an RF communication via a telecommunications tower 112 and telecommunications network 114.

The acting server 101 has a component that acts as an application server and a component that acts as a storage server. As will be appreciated these server functions may be provided by single computing device or a distributed system. The server includes one or more non-transient computer readable mediums for storing the database and for storing instructions for configuring operation of the server by executing of the instructions by one or more processors.

The storage server stores personal details about the person 103 being monitoring by the home monitoring devices 104. The application server component interfaces with the hub device 102 to control the home monitoring, and the application server may be accessed from either or both of the remote stations/devices 110(*a,b*) to enable control therefrom or to provide access to information, such as the person's details, relevant to the monitoring system. In some embodiments the monitoring station 110*a* is at the server 101, while in other embodiments it is remote from the server. In any case the monitoring station 110*a* is remote from the hub device 102.

The remote device/station may be a monitoring station 110(*a*) at which one or more people administer surveillance and responses to the surveillance, when necessary. For example, the monitoring station may be forwarded the indication of safety threat by the control panel 102, and in response a person may dispatch security personnel or an ambulance, depending on the personal details retrieved from the server 101. The monitoring station 110*a* may operate queuing software to handle messages received from the server 101, and from the queued messages output data to one or more interfaces at which people are stationed.

Another remote device/station may be provided in the form of a personal general computing device 110*b*, such as a laptop, notebook, desktop, tablet, smartphone or the like. The personal computing device may alternatively be a customized computing device intended specifically for the administration of the system 100. In any case the personal computing device may be operated by a person such as a family member or carer of the person 103.

The person 103 also carries, at least when leaving their home, a portable wireless telecommunications network enabled device 120 (e.g. using 3G, 4G/LTE or any other telecommunications protocol), e.g. a smartphone. The portable telecommunications device 120 is BLE enabled and has installed thereon on an app that configures the portable telecommunications device 120 to, upon detecting a BLE advertisement from a personal emergency device such as device 111, transmit an alert signal to the server 101.

At installation of the app, a person enters the phone number of the portable telecommunications device 120 into the app on the portable telecommunications device 120. In other embodiments, the portable telecommunications device 120 automatically reads the phone number from a SIM card in the portable telecommunications device.

Configuration of the app also involves a Bluetooth (more specifically BLE) communication to the telecommunications device 120 from the personal emergency device 111. The communication configures the app to act on broadcasted BLE advertisements from the device 111 as described herein.

Figure 2:
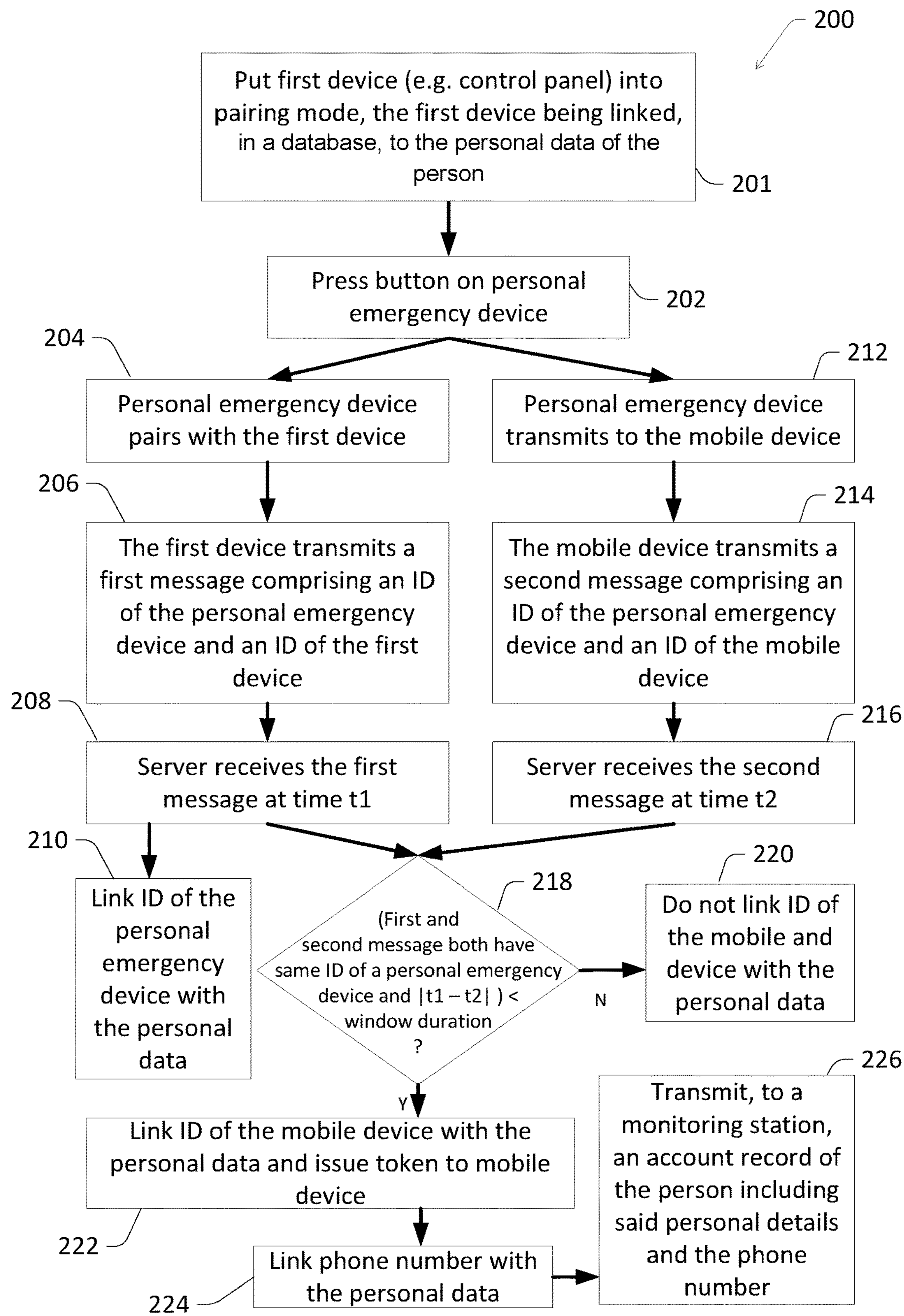
FIG. 2 shows a flowchart of one or more embodiments of a method of the invention including a configuration and registration phase.

FIG. 2 shows a flowchart of one or more embodiments of an exemplary method 200 showing configuration and registration of the system 100 for using the personal emergency device 111.

Personal details of the person 103 are recorded in a database accessible by an application layer of server 101. The personal details are stored in an electronic record that includes a first device in the form of a hub device/control panel 102 of the monitoring system 100. The person 103 has a mobile device, in this example a smartphone 120, which has the app installed, and the phone number of the mobile device 120 known by the app (e.g. by manual entering of the phone number upon installation of the app). The person 103 also has a portable, personal emergency device 111 in the form of a wearable device, e.g. a pendant, and has a fall detector and/or a panic button. Neither the personal emergency device nor the mobile device are at this stage known to the server 101.

At step 201, the person 103 puts the first device 102 into a pairing mode. At step 202, the person 103 then presses the panic button on the personal emergency device 111 which causes the personal emergency device 111 to firstly communicate with the first device 102, at step 204, and then immediately afterwards commence communicate with the mobile communications device 120, at step 212 for configuration purposes.

In each of these communication processes the personal emergency device 111 transmits a hardware identifier, which in this example is a serial number, to the respective receiving device.

Upon receiving the hardware identifier of the personal emergency device 111, the first device 102, transmits, at step 206, a first message to the server 101. The first message includes the hardware identifier of the personal emergency device 111 and an identifier of the first device 102, in this example its serial number.

At step 208, the server 101 receives the first message at time t1. At step 210, the server 101 links the hardware ID of the personal emergency device 111 with the personal data in the database. This is achieved by identifying the personal data corresponding to the received ID of the first device 102, and associating the personal data with the hardware ID of the personal emergency device 111. For example, the server may identify the personal data by referencing the received ID of the first device 102 in a write action to the database. The server may associate the personal data with the hardware ID of the personal emergency device 111 by writing the hardware ID of the personal emergency device 111 to the database in the write action, so that the hardware ID of the personal emergency device 111 is linked/associated in the database with the personal data. As will be appreciated, the link may be a direct link to the personal data or may be a link to hardware ID of the personal emergency device, which is in turn linked to the personal data.

At step 214, once the mobile device 120 receives the hardware ID of the personal emergency device, it transmits a second message to the server 101. The server may be known to the app of the mobile device 120 by, for example, a hard-coded IP address in the app, which is a fixed IP address of the server. The app has an ID that is specific to the mobile device on which it is installed. The second message identifies the personal emergency device 111 and the mobile device 120 by including in the message the hardware ID of the personal emergency device 111 and the application ID of the mobile device 120, respectively.

At step 216, the second message is received at the server 101 at time t2. Time t2 may be before or after t1, even the message from the first device 102 is transmitted prior to transmission of the message from the mobile device 120. Further, other embodiments are possible in which the messages may be transmitted in the opposite order. For either reason, the term "first message" and "second message"" as used herein is not intended to imply that the "first message" necessarily precedes the "second message" at the time or transmission and nor at the time of reception.

At step 218 the server determines server identifies that the first and second messages are intended to be associated with each other because each includes the same personal emergency device hardware ID. The server calculates the difference between t1 and t2 and compares this with a predefined threshold, which is configurable but may be, for example 2 minutes, to allow for potential delays.

If the difference is less than the threshold, then at step 222, the server 101 infers that the second message came from a device that was physically at the location of the hub first device 102, as it would be extremely unlikely that a person not having access to the first device 102 (to execute step 202) would have transmitted the hardware ID of the personal emergency device 111 during the available time window. It is thereby inferred by the server 101 that the mobile device 120 is an authorized device, and accordingly, at step 222, the application ID of the mobile device 120 is linked, in the database, to the personal data. Further, at step 222, upon determining that the mobile device is authorized, the server transmits a token to mobile device 120 to enable the mobile device 120 to later transmit an emergency event to the server, when received from the personal emergency device 111 (see step 304 below). This completes the configuration of the mobile device 120 and personal emergency device 111 at step 222.

In an event that prior to commencement of method 200, the personal emergency device has already been paired with the first device 102, there is no need to re-pair at step 204. However, if such a pairing has already occurred, step 204 nonetheless occurs in order to use a time window as described above. For such a case, step 210 is redundant since the linking of the personal emergency device 111 and the personal data is already in place.

The second message may advantageously also include the phone number of the mobile device 120. In some embodiments the phone number is also linked to the personal data at step 224. It is noted that in other embodiments the phone number may be used in place of the application ID. However, since the SIM card to which the phone number is tied may be potentially by changed, it is advantageous to provide both the phone number and the application ID to the server.

Then at step 226, the server 101 transmits an account record of the person 103, including the personal details and in some embodiments the phone number, to the monitoring station. However, in some other embodiments, the monitoring station already has an account record with the personal details of the person 103 (e.g. because of a previous transmission from the server 101). For such embodiments, the server 101 instead transmits, at step 226, a reference to identify the corresponding account of the person 103, and in some embodiments the phone number.

As shown at step 220, if it is determined at step 218 that the difference is greater than the threshold the server does not link the application ID of the mobile device 120 with the personal data. Advantageously, this may protect against a cyberattack attempting to register incorrect mobile device details.

Figure 3:
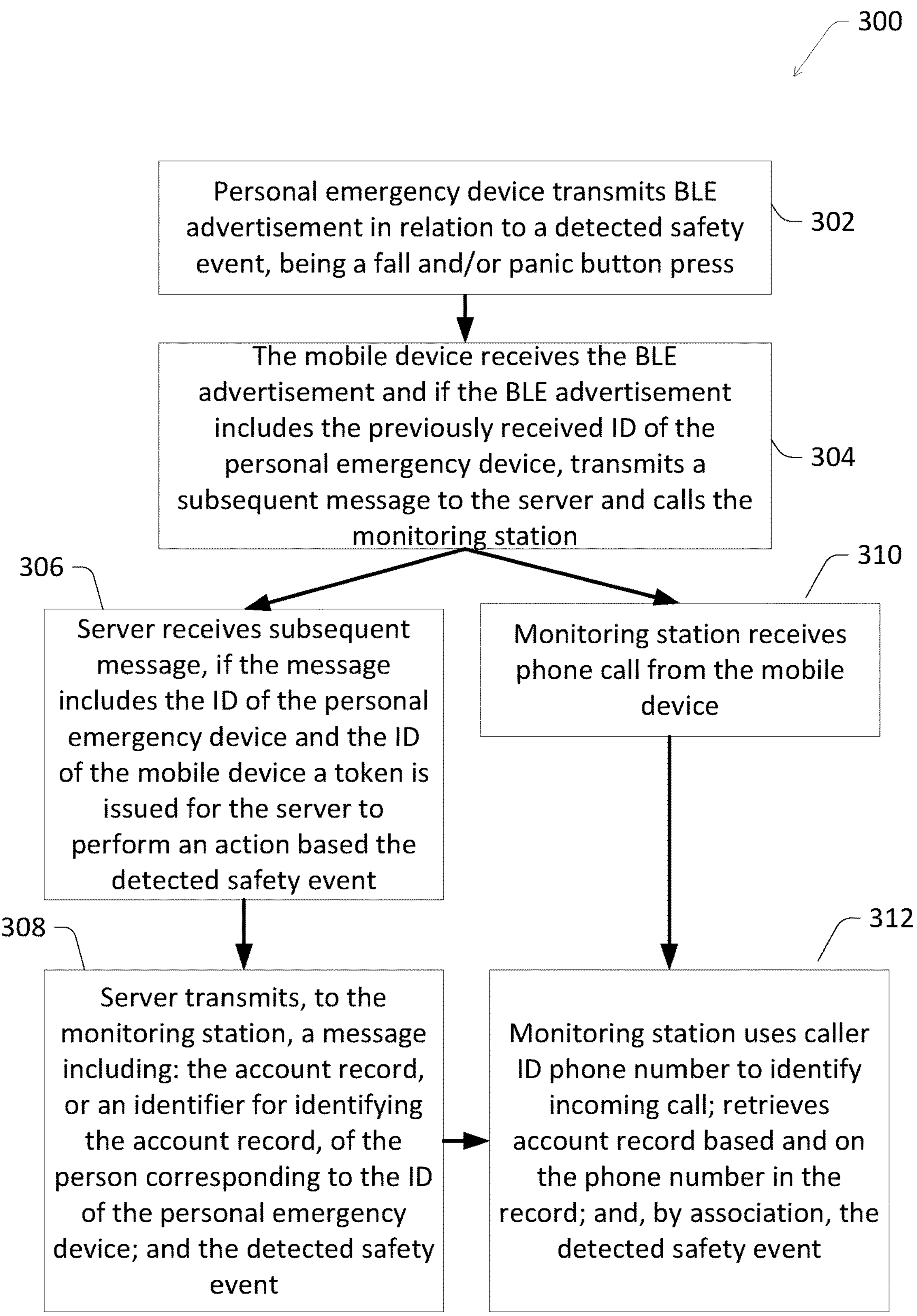
FIG. 3 shows a flowchart of one or more embodiments of an implementation or use phase.

FIG. 3 shows a flowchart of an exemplary method 300 in which the personal emergency device 111 is in use to monitor the person's safety, once it has been registered in the database, for example using the method 200. In this exemplary method the person 103 is away from their residence and, as a result, the first device 102 is unavailable to receive alerts from the personal emergency device 111.

At step 302, the personal emergency device 111 detects an emergency incident such as a fall detection or the pressing of the panic button. In response the personal emergency device 111 transmits a BLE advertisement which includes the hardware ID of the personal emergency device 111 and data about the detected event (e.g. whether it was a detected fall or panic button press).

At step 304, the mobile device 120 detects the advertisement and confirms, based on the hardware ID received in the advertisement, that it is from the previously received personal emergency device for which it was previously configured and, in the event that this is confirmed, transmits a subsequent message (e.g a third or fourth message, for example) to the server 101. The subsequent message includes an identifier of the mobile device 120 (e.g. the application ID of the mobile device 120) and the hardware ID of the personal emergency device 111, and the details of the data about the detected event, for example an event type, which may indicate a selected one or more of: a fall event and a panic event. The message may optionally also include the phone number recorded by the app.

The transmission of the subsequent message, in some embodiments, requires a valid token. A valid token was issued at step 222. However, if the server 101 in the meantime receives a valid configuration request according to step 216 of method 200 but for a different mobile device, or from the same mobile device 120 but for a different personal emergency device, then the token based on the application ID of the mobile device 120 and the hardware ID of the personal emergency device 111 will be revoked (e.g. by cancelling the ability of the server 101 to accept the previously issued token from step 222). Alternatively, the token may be temporarily revoked, for other reasons e.g. a temporary cyber-security concern. The mobile device 120 will receive a notification that its token has been revoked. At which stage the mobile device 120 can request a new token based on the mobile 120 and device 111 IDs and a new token will be issued if the token was only temporarily valid. Otherwise the mobile device can request a new token by repeating method 200.

In any case, when there is a valid token, the subsequent message (the message from the mobile device 120 in response an alert from the personal emergency device 111) is received by the server 101 at step 306.

As a result, in step 308, the server 101 transmits, to the monitoring station 110*a*, a message including: the data relating to a detected safety event (an event detected by the personal emergency device 111); and the account record of the person corresponding to the ID of the personal emergency device, or an identifier for identifying the account record (if a current account record had previously been sent, for example by step 226). In some embodiments, more specifically both the record and the identifier for identifying the record are transmitted. In other embodiments, the identifier or the record, is transmitted. At least the identifier is transmitted in some embodiments in which exists at the monitoring station prior to the transmission of that message. In embodiments in which a phone number was included in the subsequent message received by the server 101 at step 304, then the message transmitted at step 308 may optionally also include that phone number. Otherwise, the phone number may still be known, from an earlier time, e.g. because of step 226.

At 304 the mobile device 120 may also automatically make a call to the monitoring station 110*a*, the phone number of monitoring station being hard-coded into the app. The call is received by at the monitoring station at step 310. At step 312, using caller ID the monitoring station determines the phone number of the incoming call. The determined phone number is then used by the station 110*a* to retrieve from memory the relevant account record based on being received at step 226 and/or step 308. The attendant at the monitoring station may act on the call with knowledge of the persons details, without having to ask the person, who may not in any case, be able to respond.

In embodiments where caller ID is not enabled, attendant may nonetheless know who the person might be based on the information received from the server at step 308. In any case, if the call drops out after identifying the person 103, the attendant may use the information received at step 308 and/or 206 to call back the person 103. Further if no call is received, the attendant can initiate a call to the person 103 based on the information received from the server at step 308.

As will be appreciated the server 101 uses the hardware ID of the personal emergency device to access the personal details of the person 103 by executing step 226 or step 308 or both. Thus, the personal details are accessed by receipt of the second message or a subsequent message including the hardware ID of the personal emergency device.

As will be appreciated, the phrase "hardware ID" of a device is intended to refer to an ID transmittable from the device to identify the device. It may be defined however by software which writes the ID to a memory on the device, or it may be hardcoded into the device. As will be therefore be appreciated, the exemplified IDs of mobile device 120 and the first device 102 are therefore also "hardware IDs", even though in the case of a software implemented ID the ID may be changed by an active/deliberate interaction, such as deleting and reinstalling the app.

Where a given item is referenced herein with the preposition "a" or "an", it is not intended to exclude the possibility of additional instances of such an item, unless context requires otherwise.

Where the specification defines a range, the stated outer extremities of the range are part of the range, unless context requires exclusion of the outer extremities from the range. From example, a range defined in terms of being between X and Y or from X to Y, should be interpreted as including X and Y.

The invention disclosed and defined herein extends to all plausible combinations of two or more of the individual features mentioned or evident from the text or drawings. All of these different combinations constitute various alternative aspects of the invention.

What is claimed is:

1. A method of identifying to a monitoring station personal data of a person in response to a use of a personal emergency alert device, wherein the personal data is linked, in a server, to a first device, the method comprising:

a. receiving, at the server, a first message comprising an ID of the first device and a hardware ID of the personal emergency device;

b. linking, at the server, the personal emergency device with the personal data, by:

i. identifying the personal data corresponding to the received ID of the first device, and ii. associating the personal data with the hardware ID of the personal emergency device, c. receiving, at the server, a second message from a mobile device comprising the hardware ID of the personal emergency device and an ID of the mobile device;

d. at the server, associating the personal data with the ID of the mobile device; and e. in response to at least one of (i) receipt of the second message, and (ii) receipt of a subsequent message received at the server via the mobile device and comprising the hardware ID of the personal emergency device and the ID of the mobile device, transmitting, by the server, a message to the monitoring station, wherein based on the prior association of the personal data with the hardware ID of the personal emergency device the server includes in the message (i) the personal data or (ii) an identifier for identifying said personal data.

2. The method of claim 1 wherein the mobile ID is an application ID of a monitoring application installed on the mobile device, a hardware ID of the mobile device, or a mobile number of the mobile device.

3. The method of claim 1 wherein first and second messages are received within a time window of a predetermined duration to enable step (d).

4. The method of claim 1 wherein the first device is a control panel.

5. The method of claim 1 wherein the first message is received from the first device.

6. The method of claim 1 wherein the personal emergency device is a battery operated wearable device, and the personal emergency device wirelessly communicates with the first device in a pairing process that triggers said first message from the first device.

7. The method of claim 1 wherein the personal emergency device communicates with the mobile device via a Bluetooth communication to trigger transmission of said second message to the server from the mobile device.

8. The method of claim 1 wherein the personal emergency device is configured to, in response to detecting a fall or panic event, transmit a Bluetooth signal which includes the hardware ID of the personal emergency device for receipt by mobile device for the mobile device to transmit said subsequent message to the server.

9. A system for identifying personal data of a person in response to a use of a personal emergency alert device, wherein the personal data is linked, in a server, to a first device, the system including the server, the server being programmed to:

a. receive a first message comprising an ID of the first device and a hardware ID of the personal emergency device, b. link the personal emergency device with the personal data, said linking including:

i. identifying the personal data corresponding to the received ID of the first device, and ii. associating the personal data with the hardware ID of the personal emergency device, c. receive a second message from a mobile device comprising the hardware ID of the personal emergency device and an ID of the mobile device;

d. associate the personal data with the ID of the mobile device; and e. in response to at least one of (i) receipt of the second message, and (ii) receipt of a subsequent message received via the mobile device and comprising the hardware ID of the personal emergency device and the ID of the mobile device, transmitting a message to the monitoring station, wherein based on the prior association of the personal data with the hardware ID of the personal emergency device the server includes in the message (i) the personal data or (ii) an identifier for identifying said personal data.

10. The system of claim 9 wherein the mobile ID is an application ID of a monitoring application installed on the mobile device, a hardware ID of the mobile device, or a mobile number of the mobile device.

11. The system of claim 9 wherein first and second messages are received within a time window of a predetermined duration to enable step (d).

12. The system of claim 9 which includes the first device, the first device including a control panel which is part of a home monitoring system.

13. The system of claim 9 wherein the first message is received from the first device.

14. The system of claim 9 wherein the system includes the personal emergency alert device.

15. The system of claim 9 wherein the system includes a computer readable medium storing a plurality of instructions which when executed by a smartphone configure the smartphone to act as said mobile device.

16. A computer product comprising one or more non-transient computer readable mediums storing a plurality of instructions which when executed by a server cause the server to:

a. receive a first message comprising an ID of the first device and a hardware ID of the personal emergency device, b. link the personal emergency device with the personal data, said linking including:

i. identifying the personal data corresponding to the received ID of the first device, and ii. associating the personal data with the hardware ID of the personal emergency device, c. receive a second message from a mobile device comprising the hardware ID of the personal emergency device and an ID of the mobile device;

d. associate the personal data with the ID of the mobile device; and e. in response to at least one of (i) receipt of the second message, and (ii) receipt of a subsequent message received via the mobile device and comprising the hardware ID of the personal emergency device and the ID of the mobile device, transmitting a message to the monitoring station wherein based on the prior association of the personal data with the hardware ID of the personal emergency device the server includes in the message (i) the personal data or (ii) an identifier for identifying said personal data.

17. The method of claim 1, wherein the subsequent message received from the mobile device must comprise the hardware ID of the personal emergency device and the ID of the mobile device for the server to transmit said message to the monitoring station in response to receiving the subsequent message.

18. The system of claim 9, wherein the subsequent message received from the mobile device must comprise the hardware ID of the personal emergency device and the ID of the mobile device for the server to access the personal data in response to the subsequent message.

* * * * *